US005622980A

United States Patent [19]
Caldwell et al.

[11] Patent Number: 5,622,980
[45] Date of Patent: Apr. 22, 1997

[54] ORAL COMPOSITIONS OF H2-ANTAGONISTS

[75] Inventors: Henry C. Caldwell, Ambler, Pa.; Ashok J. Desai, Wilmington, N.C.

[73] Assignee: Applied Analytical Industries, Inc., Wilmington, N.C.

[21] Appl. No.: 382,602

[22] Filed: Feb. 2, 1995

Related U.S. Application Data

[63] Continuation-in-part of Ser. No. 288,711, Aug. 12, 1994, abandoned, which is a continuation-in-part of Ser. No. 107,126, Aug. 17, 1993, abandoned.

[51] Int. Cl.$^6$ .................. A61K 31/425; A61K 31/415; A61K 31/34; A61K 33/12; A61K 33/06; A61K 33/08

[52] U.S. Cl. .................. 514/370; 514/400; 514/471; 424/683; 424/684; 424/687

[58] Field of Search .................. 514/370, 400, 514/471; 424/683, 684, 43, 44, 687

[56] References Cited

U.S. PATENT DOCUMENTS

| | | | |
|---|---|---|---|
| 3,140,978 | 7/1964 | Zentner | 167/55 |
| 3,248,290 | 4/1966 | Zentner | 167/55 |
| 3,337,402 | 8/1967 | Zentner | 167/55 |
| 3,337,403 | 8/1967 | Zentner | 167/55 |
| 3,427,379 | 2/1969 | Barry et al. | 424/14 |
| 3,432,593 | 3/1969 | Shepard | 424/20 |
| 3,567,819 | 3/1971 | Idson et al. | 424/16 |
| 4,327,076 | 4/1982 | Puglia et al. | 424/38 |
| 4,711,774 | 12/1987 | Denick, Jr. et al. | 424/48 |
| 4,716,033 | 12/1987 | Denick, Jr. | 424/48 |
| 4,717,565 | 1/1988 | Denick, Jr. et al. | 424/155 |
| 4,719,228 | 1/1988 | Rawlins | 514/456 |
| 4,753,800 | 6/1988 | Mozda | 424/440 |
| 4,758,424 | 7/1988 | Denick, Jr. et al. | 424/48 |
| 4,758,425 | 7/1988 | Denick, Jr. et al. | 424/48 |
| 4,761,274 | 8/1988 | Denick, Jr. et al. | 424/48 |
| 4,859,709 | 8/1989 | Rawlins | 514/770 |
| 5,057,319 | 10/1991 | Gottwald et al. | 424/441 |
| 5,075,114 | 12/1991 | Roche | 424/470 |
| 5,084,278 | 1/1992 | Mehta | 424/441 |
| 5,169,640 | 12/1992 | France et al. | 424/470 |
| 5,183,829 | 2/1993 | Caldwell | 514/570 |
| 5,188,839 | 2/1993 | Pearmain | 424/464 |
| 5,204,118 | 4/1993 | Goldman et al. | 424/489 |
| 5,213,794 | 5/1993 | Fritsch et al. | 424/78.01 |
| 5,219,563 | 6/1993 | Douglas et al. | 424/78.1 |
| 5,225,197 | 7/1993 | Bolt et al. | 424/440 |
| 5,229,137 | 7/1993 | Wolfe | 424/687 |
| 5,260,072 | 11/1993 | Roche et al. | 424/464 |
| 5,275,823 | 1/1994 | France et al. | 424/489 |
| 5,288,506 | 2/1994 | Spickett et al. | 424/498 |

FOREIGN PATENT DOCUMENTS

| | | |
|---|---|---|
| 2222772 | 3/1990 | United Kingdom. |
| WO92/00102 | 1/1992 | WIPO. |
| WO93/24124 | 12/1993 | WIPO. |
| WO94/08560 | 4/1994 | WIPO. |
| WO94/08576 | 4/1994 | WIPO. |

OTHER PUBLICATIONS

K. M. Koch, Abstract, Effect of Sapp on Ranitidine Bioavailability and Gastrointestinal Transit Time; *Pharmaceutical Research* 9:10, PPDM 8269, p. S–324 (1992).

J. T. Carstensen et al; Nature of Bonding in Montmorillonite Adsorbates I: Surface Adsorption; *Journal of Pharmaceutical Sciences* 60 pp. 733–735 (1971).

J. W. McGinity et al.; in Vitro Adsorption of Various Pharmaceuticals to Montmorillonite; *Journal of Pharmaceutical Sciences* pp. 896–902. (1980).

K. M. Koch et al.; Effect of Sodium Acid Pyrophosphate on Ranitidine Bioavailability and Gastrointestinal Transit Time; *Pharmaceutical Research* 10 pp. 1027–1030 (1993).

J. W. McGinity et al.; Influence of Monovalent and Divalent Electrolytes on Sorption of Neomycin Sulfate to Attapulgite and Montmorillonite Clays; *Journal of Pharmaceutical Sciences* 64 pp. 1566–1568 (1975).

K. Munzel; The Desorption of Medicinal Substances from Adsorbents in Oral Pharmaceutical Suspensions; *Acta Pharmacologia Et Toxicologica* 29 Suppl 3, (Copenh) (Denmark) pp. 81–87(1971).

J. W. McGinity et al.; Influence of Montmorillonite Clay on The Properties of Griseofulvin Tablets; *Drug Development and Industrial Pharmacy* 6(1), pp. 49–59 (1980).

J. W. McGinity et al.; Optimization of Slow–release Tablet Formulations Containing Montmorillonite 1. Properties of Tablets, *Drug Development and Industrial Pharmacy*, 6(4), pp. 399–410 (1980).

J. W. McGinity et al.; Sustained–Release Application of Montmorillonite Interaction with Amphetamine Sulfate, *Journal of Pharmaceutical Sciences* 66(1) pp. 63–66 (1977).

Primary Examiner—Raymond Henley, III
Attorney, Agent, or Firm—Bell, Seltzer, Park & Gibson

[57] ABSTRACT

The present invention provides a pharmaceutical composition for the oral administration of an $H_2$-antagonist. The composition includes an $H_2$-antagonist and a silicate taste-masking agent capable of forming an adsorbate complex with the $H_2$-antagonist wherein the complex exhibits a non-bitter taste. The complex inhibits the release of the $H_2$-antagonist in the oral cavity.

15 Claims, No Drawings

ORAL COMPOSITIONS OF H2-ANTAGONISTS

RELATED APPLICATIONS

This application is a continuation-in-part of U.S. application Ser. No. 08/288,711, filed Aug. 12, 1994, now abandoned, which is a continuation-in-part of U.S. application Ser. No. 08/107,126, filed Aug. 17, 1993, now abandoned.

FIELD OF THE INVENTION

The present invention relates to pharmaceutical compositions containing as the active ingredient, an $H_2$-antagonist, and more particularly to pharmaceutical compositions useful for the oral administration of a therapeutically effective amount of an $H_2$-antagonist.

BACKGROUND OF THE INVENTION

The $H_2$-antagonist agents (hereinafter "$H_2$-antagonists") are routinely administered orally to patients suffering from gastrointestinal conditions such as ulcers, dyspepsia, various reflux indications and the like. Typically, the $H_2$-antagonist is delivered to the patient in tablet or powder-filled capsule form. Other liquid oral compositions such as syrups have also been proposed (see, for example, U.S. Pat. No. 4,128,658 to Price et al.)

The $H_2$-antagonists are known to have an unpalatably bitter taste when ingested in any form other than solid capsule or tablet form. However, certain segments of the patient population prefer more easily ingested product forms, including chewable tablets, lozenges or troches. Several attempts, with somewhat limited success, have been made to produce a pharmaceutical composition for oral administration which contains an $H_2$-antagonist. For example, U.S. Pat. No. 5,219,563 to Douglas et al. proposes drug adsorbates for masking the bitter taste of ranitidine which include synthetic cation exchange resins. PCT Publication No. WO 94/0856 to Glaxo proposes chewable tablets of ranitidine, which include an intense sweetener such as aspartame. PCT Publication No. WO94/08576 to Glaxo proposes taste-masked compositions of ranitidine comprising a dispersion of lipid coated ranitidine particles in a non-aqueous vehicle. U.S. Pat. No. 5,260,072 to Roche et al. proposes chewable tablets of $H_2$-antagonists which contain retrogranules of the drug coated with cellulose acetate, cellulose acetate butyrate or a combination thereof to mask the taste of the $H_2$-antagonist. U.S. Pat. No. 5,084,278 to Mehta proposes taste-masked ranitidine chewable tablets containing a medicinal core coated with a polymeric coating. U.S. Pat. No. 5,275,823 to France et al. proposes chewable tablets of cimetidine contaiing hygroscopic water-insoluble substances, such as polysaccharides, as extragranular excipients.

Attempts at taste-masking other pharmaceutical agents have also been proposed. For example, U.S. Pat. No. 4,711,774 to Denick, Jr. et al. proposes a magnesium aluminum silicate as an adsorbate for analgesics, antiasthmatics, antitussives, antihistamines, and other drugs. U.S. Pat. No. 3,140,978 to Zentner also proposes magnesium aluminum silicate pharmaceutical compositions. Neither of these references discloses or suggests masking the bitter taste of an $H_2$-antagonist with aluminum magnesium silicate.

Accordingly, there remains a need in the art for methods of taste-masking $H_2$-antagonists for the preparation of oral dosage units containing the same. Moreover, there remains a need in the art for pharmaceutical compositions for the oral administration of $H_2$-antagonists.

SUMMARY OF THE INVENTION

The present invention provides a pharmaceutical composition for the oral administration of an $H_2$-antagonist. The composition includes an $H_2$antagonist and a taste-masking agent capable of forming an adsorbate complex with the $H_2$-antagonist wherein the complex exhibits a non-bitter taste. The complex inhibits the release of the $H_2$-antagonist in the oral cavity. The taste-masking agent generally comprises a silicate. As used herein, the term "silicate" refers to any of various forms of natural and synthetic clays having one or more Si-O groups in its molecular structure. In one preferred embodiment, the taste-masking agent is magnesium aluminum silicate.

The composition is preferably provided in the form of an oral dosage unit, such as a chewable or frangible tablet, a lozenge, or granules for oral administration to a patient in need thereof. The adsorbate complex masks the bitter taste of the $H_2$-antagonist such that the pharmaceutical composition does not exhibit any bitter taste to the patient.

DETAILED DESCRIPTION OF THE INVENTION $H_2$-antagonists are derivatives of histamine that bind to and exhibit inhibiting or blocking activity against H2 receptors. The $H_2$-antagonists, or "$H_2$-blocking agents," are a discrete and limited group of medications readily recognized in the art, and are generally polar, hydrophilic molecules. See, Goodman and Gilman's *The Pharmacological Basis of Therapeutics*, 7th ed. pp 624–625 (1985). Most pharmaceutical formulations which employ $H_2$-antagonists, however, have an unpalatably bitter taste. Examples of $H_2$-antagonists include but are not limited to ranitidine, cimetidine, nizatidine, famotidine, sufotidine, roxatidine, bisfentidine, tiotidine, lamtidine, niperotidine, mifentidine, zaltidine, and loxtidine. $H_2$-antagonists that are imidazole derivatives (e.g., cimetidine) and furan derivatives (e.g., ranitidine) are preferred. Ranitidine is currently most preferred.

The pharmaceutically active agents useful in the present invention are preferably provided in the form of a pharmaceutically acceptable salt or a free base. Suitable salts are readily available and well known in the art. The preferred pharmaceutically acceptable salts are water soluble. The $H_2$-antagonists may be provided in a variety of water-soluble salt forms. Suitable water soluble salt forms include hydrochloride salts, hydrobromide salts, sulfate salts, nitrate salts, citrate salts and tartrate salts. The hydrochloride salts are currently preferred.

The amount of $H_2$-antagonist, either in salt form or free base, which is included in the composition of the present invention will be dependent upon the pharmaceutical activity of the particular compound. Generally, the amount of $H_2$-antagonist is sufficient to deliver a therapeutically effective dose to a patient in need thereof. For example, the amount of $H_2$-antagonist typically included in the composition is between about 5 to about 50 percent by weight. Preferably, the amount of $H_2$-antagonist included in the composition is sufficient to provide an oral dosage form containing between about 5 to about 20 percent by weight of $H_2$-antagonist.

The taste-masking agents employed in the compositions of the present invention include any silicate capable of forming a taste-masked adsorbate complex with the $H_2$-antagonist to eliminate or reduce the bitter taste. The complex inhibits the release of the $H_2$-antagonist in the oral cavity. Examples of silicates capable of forming adsorbate complexes with $H_2$-antagonists include but are not limited to, montmorillonite, attapulgite, magnesium aluminum silicate and other clays. The preferred silicate taste-masking agent is magnesium aluminum silicate. An exemplary magnesium aluminum silicate is sold under the tradename VEEGUM™, by R. T. Vanderbilt Company, Inc. The adsorbate complex formed between the taste-masking agent and the $H_2$-antagonist masks the typically strong bitter taste of the $H_2$-antagonist while the composition is in the oral cavity. The complex is dissociated in the gastrointestinal tract to advantageously release the $H_2$-antagonist therein.

The amount of silicate taste-masking agent incorporated into the compositions is generally sufficient to form an adsorbate complex with the $H_2$-antagonists, to provide a composition having a non-bitter taste. Preferably, the silicate taste-masking agent is provided in excess, to ensure that no free or uncomplexed $H_2$-antagonist remains in the composition. Typically, the taste-masking agent is provided in an amount ratio to $H_2$-antagonist of between about 1 to about 10:1 taste masking agent to $H_2$-antagonist. Preferably, the ratio of taste-masking agent to $H_2$-antagonist is about 5:1.

The adsorbate complex of the $H_2$-antagonist and the taste-masking agent may be released from the pharmaceutical composition in the oral cavity, however, the complex inhibits the release of the $H_2$-antagonist in the oral cavity, thereby masking the typical bitter taste of the $H_2$-antagonist. Advantageously, the complex is readily dissociated, and the $H_2$-antagonist released, in the gastrointestinal tract. To further facilitate the release of the $H_2$-antagonist in the gastrointestinal tract, the composition of the present invention may also include a dissociation agent, which is capable of assisting in the dissociation of the adsorbate complex in the gastrointestinal tract.

Suitable dissociation agents will be known to those skilled in the art, but preferably include a weak base. Specific examples of suitable dissociation agents include but are not limited to, sodium bicarbonate, calcium carbonate, potassium carbonate, and the like. Calcium carbonate is the preferred dissociation agent. The amount of dissociation agent included in the composition is between about 0 and about 35 percent by weight of the composition. Preferably, the dissociation agent is included in an amount of between about 5 and about 20 percent by weight of the composition.

As will be known in the art, the pharmaceutical composition of the present invention may also include other excipients commonly employed for the formation of a variety of dosage unit forms. For example, the pharmaceutical composition of the present invention may include a pharmaceutically acceptable carrier such as microcrystalline cellulose or lactose, flavoring agents and/or sweeteners, artificial colorings, tableting excipients such as bulking agents and/or granulating agents, buffering agents, lubricants, preservatives, and the like. Suitable flavoring agents and sweeteners, include natural and artificial flavorings such as citric acid, maleic acid, tartaric acid, xylitol, mannitol, saccharin, sugar, sorbitol, maltitol, and the like. Preferred flavoring agents including citric acid, maleic acid, tartaric acid, xylitol, and mannitol. Suitable bulking agents include mannitol, xylitol, and microcrystalline cellulose. Xylitol and mannitol are particularly preferred as sweetening and bulking agents. Suitable lubricants include magnesium stearate.

The composition is preferably provided in the form of an oral dosage unit, such as a chewable or frangible tablet, a lozenge, or granules for oral administration to a patient in need thereof. According to one preferred embodiment, the pharmaceutical composition of the present invention is provided in the form of a chewable tablet. A suitable chewable tablet formulation will include between about 5 and about 20 percent by weight of the pharmaceutical composition of the present invention, and conventional chewable tablet excipients such as those described in U.S. Pat. No. 5,225,197 to Bolt et al., the disclosure of which is incorporated herein by reference in its entirety.

The pharmaceutical compositions of the present invention may be prepared using conventional oral dosage form equipment. According to one preferred method, the pharmaceutical composition may be prepared by dry mixing a pharmaceutically acceptable salt of the $H_2$-antagonist and the taste-masking agent to provide a substantially uniform admixture. Thereafter sufficient water is added to form a substantially uniform wet mass. The $H_2$-antagonist is solubilized by the added water, and the adsorbate complex forms readily, in situ. Thereafter, the wet mass is dried according to conventional techniques, and if necessary, the resulting powder is milled to achieve the desired particle size. Optionally, a predetermined quantity of a dissociation agent may be incorporated into the composition by dry mixing the dissociation agent and the dried pharmaceutical composition after milling. Other pharmaceutical excipients, as described above, may be added after milling to form the oral dosage unit. The oral dosage unit may then be compressed into tablet form to provide a chewable tablet.

According to a second preferred embodiment, the pharmaceutical composition of the present invention may be prepared by dry mixing the free base of the $H_2$-antagonist and the taste-masking agent to provide a substantially uniform admixture. Thereafter a sufficient quantity of dilute acid, such as hydrochloric acid is added to form a substantially uniform wet mass. The $H_2$-antagonist is solubilized by the added acid, and the adsorbate complex forms readily, in situ. Thereafter, the oral dosage form may be prepared according to the steps outlined above.

One skilled in the art will appreciate that other excipients may be employed, and other oral dosage forms may be prepared using techniques which are well known in the art. Accordingly, one skilled in the art will appreciate that the present invention contemplates the preparation of such dosage forms.

The daily dose of any particular $H_2$-antagonist may be provided in the form of one or more oral dosage units containing the pharmaceutical composition according to the present invention. The daily dose of the $H_2$-antagonist is non-toxic and therapeutically effective. Typically, the daily dose of $H_2$-antagonist is from 40 to 1600 mg, depending upon the particular $H_2$-antagonist to be administered. For example, the suggested daily dose of ranitidine and nizatidine is 300 mg, cimetidine is 800 mg, and famotidine is 40 mg. See, Histamine and Histamine antagonists, *Handbook Exp. Pharmacol.* 97: 573 (1991), the disclosure of which is incorporated herein by reference in its entirety. The oral dosage unit may include a dose of from 10 to 800 mg of $H_2$-antagonist, depending on the known pharmaceutical activity and market of the $H_2$-antagonist drug. Typically, the dosage units are administered orally from 1 to 5 times daily.

The following examples are provided to illustrate the present invention, and should not be construed as limiting thereof.

EXAMPLE 1

This example shows the preparation of chewable tablets. The ingredients are shown in Table 1.

TABLE 1

| Ingredients | % By Weight | | | |
|---|---|---|---|---|
| | A | B | C | D |
| Nizatidine | 5 | — | — | — |
| Cimetidine | — | 5 | — | — |
| Ranitidine | — | — | 5 | — |
| Famotidine | — | — | — | 2 |
| Magnesium Aluminum Silicate NF | 25 | 25 | 25 | 10 |
| Sodium Saccharin NF | .25 | .25 | .25 | .125 |
| Mannitol NF | Q.S. | Q.S. | Q.S. | Q.S. |
| Xylitol NF | Q.S. | Q.S. | Q.S. | Q.S. |
| Collodial Silicon Dioxide NF | 1 | 1 | 1 | 1 |
| Magnesium Stearate NF | 1.5 | 1.5 | 1.5 | 1.5 |
| Flavors | Q.S. | Q.S. | Q.S. | Q.S. |
| Purified water* | | | | |
| | 100 | 100 | 100 | 100 |

*Remove during processing

Method of Manufacturing
1. Mix drug with magnesium aluminum silicate and sodium saccharin in a planetary mixer for five minutes.
2. Add water until a uniform granulation occurs.
3. Dry the granules.
4. Size the granules into fine powder.
5. Add mannitol, xylitol and collodial silicon dioxide and mix for ten minutes.
6. Add magnesium sterate and mix for five minutes.
7. Compress into chewable tablets.

EXAMPLE 2

This example shows the preparation of chewable tablets. The ingredients are shown in Table 2.

TABLE 2

| Ingredients | % By Weight | | | |
|---|---|---|---|---|
| | A | B | C | D |
| Nizatidine | 5 | — | — | — |
| Cimetidine | — | 5 | — | — |
| Ranitidine HCl USP | — | — | 5.6 | — |
| Famotidine | — | — | — | 2 |
| Magnesium Aluminum Silicate NF | 25 | 25 | 25 | 10 |
| Calcium Carbonate USP | 5 | 5 | 5 | 5 |
| Sodium Saccharin NF | .25 | .25 | .25 | .125 |
| Mannitol NF | Q.S. | Q.S. | Q.S. | Q.S. |
| Xylitol NF | Q.S. | Q.S. | Q.S. | Q.S. |
| Collodial Silicon Dioxide NF | 1 | 1 | 1 | 1 |
| Magnesium Stearate NF | 1.5 | 1.5 | 1.5 | 1.5 |
| Flavors | Q.S. | Q.S. | Q.S. | Q.S. |
| Purified water* | | | | |
| | 100 | 100 | 100 | 100 |

*Remove during processing

Method of Manufacturing
1. Mix drug with magnesium aluminum silicate and sodium saccharin in a planetary mixer for five minutes.
2. Add water until a uniform granulation occurs.
3. Dry the granules.
4. Size the granules into fine powder.
5. Add mannitol, xylitol, calcium carbonate, collodial silicon dioxide and mix for ten minutes.
6. Add magnesium sterate and mix for five minutes.
7. Compress into chewable tablets.

If the operator wishes an acid agent such as a fruit acid, for example, citric, malic or tartaric acid in the formulation, this is added to the manufacturing process at Step 1 before the granulation process, usually at about 1.5%.

The following comparative examples were selected to illustrate the enhanced release of active ingredient from the granules/tables of this invention using the preparative and testing procedures described above.

EXAMPLE 3

Comparative Example

The percentage of cimetidine dissolved in water using the U.S.P. method II at 50 RPM to 60 minutes from granules with added citric acid (3%), calcium carbonate (75 mg) and without calcium carbonate.

TABLE 3

| Time (min.) | Without $CaCO_3$ | With $CaCO_3$ |
|---|---|---|
| 15 | 39.9 | 67.5 |
| 30 | 44.6 | 74.4 |
| 45 | 46.9 | 78.8 |
| 60 | 48.3 | 82.8 |
| 75 | 51.6 | 104.3 |

EXAMPLE 4

Comparative Example

Ranitidine Hydrochloride (75 mg base) with Calcium Carbonate (75 mg)

TABLE 4

| Time (min.) | Without $CaCO_3$ | With $CaCO_3$ |
|---|---|---|
| 15 | 30.3% | 44.0% |
| 30 | 36.6% | 51.4% |
| 45 | 36.9% | 53.7% |
| 60 | 37.6% | 56.8% |
| | 40.4% | 63.6% |

EXAMPLE 5

Comparative Example

Nizatidine with and without calcium carbonate compared at 0 time and 1 month stability (40°; 75% RH), citric acid (1.5%) added to all samples.

TABLE 5

| Time (min.) | Without $CaCO_3$ | Stability | With $CaCO_3$ | Stability |
|---|---|---|---|---|
| 15 | 30.3 | 30.0 | 77.6 | 45.7 |
| 30 | 34.8 | 34.5 | 82.3 | 60.3 |
| 45 | 36.6 | 37.42 | 84.2 | 67.2 |
| 60 | 38.8 | 39.4 | 85.3 | 70.0 |
| 75 | 42.9 | 44.1 | 94.4 | 90.3 |

EXAMPLE 6

Comparative Example

Nizatidine granules compared in water with tablet with 1.5% citric acid and tablet with 1.5% of citric acid and 37.5 mg of calcium carbonate.

TABLE 6

| Time (min.) | Gran | Tab (1.5% C.A.) | Tab (C.A. plus CaCO$_3$) |
|---|---|---|---|
| 0 | 0 | 0 | 0 |
| 30 | 88.8 | 39.1 | 97 |

EXAMPLE 7

Comparative Example

The process of Example 1 is used with 25% by weight of magnesium aluminum slicate, 5% of nizatidine, 0.25% of sodium saccharin and 1.2% of citric acid. The granules, before tabletting, were compared with the tabletted product and with the chewable tablet with 5% of calcium carbonate.

TABLE 7

| Time | Gran | (Without CaCO$_3$) | (With CaCO$_3$) |
|---|---|---|---|
| 0 | 0 | 0 | 0 |
| 30 | 37 | 45 | 92.2 |
| 60 | 39.2 | 47 | 93 |
| 75 | 47.4 | 47.4 | 95.7 |

The foregoing is illustrative of the present invention and is not to be construed as limiting thereof. The invention is defined by the following claims, with equivalents of the claims to be included therein.

That which is claimed is:

1. A pharmaceutical composition for the oral administration of a therapeutically effective amount of an H$_2$-antagonist, wherein said composition exhibits a non-bitter taste, said composition consisting essentially of an H$_2$-antagonist, a silicate taste-masking agent capable of forming an adsorbate complex with said H$_2$-antagonist, wherein said complex inhibits the release of the H$_2$-antagonist in the oral cavity, and between about 2.5 and about 10 percent based upon the weight of the composition of a dissociation agent capable of enhancing the release of said H$_2$-antagonist from said adsorbate complex, wherein said dissociation agent comprises calcium carbonate.

2. The pharmaceutical composition according to claim 1, wherein said silicate taste-masking agent comprises magnesium aluminum silicate.

3. The pharmaceutical composition according to claim 1, wherein said H$_2$-antagonist is in the form of a pharmaceutically acceptable salt.

4. The pharmaceutical composition according to claim 1, wherein said H$_2$-antagonist is in the form of a free base.

5. The pharmaceutical composition according to claim 1 further including a flavoring agent.

6. The pharmaceutical composition according to claim 5, wherein said flavoring agent is selected from the group consisting of citric acid, maleic acid, tartaric acid, mannitol, xylitol, sugar, sorbitol, maltitol, and saccharin.

7. The pharmaceutical composition according to claim 1, wherein said H$_2$-antagonist is selected from the group consisting of nizatidine, famotidine, ranitidine, and cimetidine.

8. The pharmaceutical composition according to claim 1, further including a pharmaceutically acceptable carrier.

9. The pharmaceutical composition according to claim 8 in the form of a chewable tablet.

10. The pharmaceutical composition according to claim 8 in the form of a lozenge.

11. The pharmaceutical composition according to claim 8 in the form of granules.

12. The pharmaceutical composition according to claim 1, wherein said calcium carbonate dissociation agent is present in an amount of about 5 percent based upon the weight of the composition.

13. A pharmaceutical composition for the oral administration of a therapeutically effective amount of an H$_2$-antagonist, wherein said composition exhibits a non-bitter taste, said composition comprising a non-bitter tasting adsorbate complex of ranitidine hydrochloride and magnesium aluminum silicate, and a dissociation agent consisting of calcium carbonate.

14. A pharmaceutical composition for the oral administration of a therapeutically effective amount of an H$_2$-antagonist, wherein said composition exhibits a non-bitter taste, said composition comprising a non-bitter tasting adsorbate complex of ranitidine hydrochloride and magnesium aluminum silicate, a dissociation agent consisting of calcium carbonate, and an a flavoring agent selected from the group consisting of citric acid and xylitol.

15. A method for enhancing the release of an H$_2$-antagonist from an oral pharmaceutical formulation comprising an adsorbate complex, said adsorbate complex consisting essentially of a therapeutically effective amount of an H$_2$-antagonist and a silicate taste-masking agent, said method comprising incorporating into said pharmaceutical formulation a dissociation agent that enhances the release of said H$_2$-antagonist from said adsorbate complex, wherein said dissociation agent comprises calcium carbonate.

* * * * *